United States Patent [19]

Berg et al.

[11] Patent Number: 4,690,734
[45] Date of Patent: Sep. 1, 1987

[54] SEPARATION OF N-AMYL ACETATE FROM N-AMYL ALCOHOL BY EXTRACTIVE DISTILLATION

[76] Inventors: Lloyd Berg; An-I Yeh, both of 1314 S. Third Ave., Bozeman, Mont. 59715

[21] Appl. No.: 801,214

[22] Filed: Nov. 25, 1985

[51] Int. Cl.⁴ .......................... B01D 3/40; C07C 67/48
[52] U.S. Cl. ........................................ 203/56; 203/57; 203/60; 203/64; 560/248
[58] Field of Search .................... 203/56, 64, 57, 60, 203/14, 18; 568/913; 560/248

[56] References Cited

U.S. PATENT DOCUMENTS

| | | | |
|---|---|---|---|
| 2,489,619 | 11/1949 | Carlson et al. | 203/73 |
| 2,559,519 | 7/1951 | Smith et al. | 203/64 |
| 2,559,520 | 7/1951 | Smith et al. | 203/64 |
| 2,575,285 | 11/1951 | Carlson et al. | 203/56 |
| 4,379,028 | 4/1983 | Berg et al. | 203/64 |
| 4,431,838 | 2/1984 | Feldman et al. | 203/84 |

FOREIGN PATENT DOCUMENTS

| | | | |
|---|---|---|---|
| 1088040 | 9/1960 | Fed. Rep. of Germany | 203/64 |
| 815774 | 7/1959 | United Kingdom | 560/248 |

Primary Examiner—Wilbur Bascomb

[57] ABSTRACT n-Amyl acetate cannot be completely removed from n-amyl acetate - n-amyl alcohol - water mixtures by distillation because of the presence of the minimum ternary azeotrope. n-Amyl acetate can be readily removed from mixtures containing it, n-amyl alcohol and water by using extractive distillation in which the extractive distillation agent is a higher boiling organic compound or a mixture of these. Typical examples of effective agents are ethylene glycol; propylene glycol and dimethylsulfoxide; 1,3-butanediol, dimethylformamide and acetamide.

30 Claims, No Drawings 4,690,734

SEPARATION OF N-AMYL ACETATE FROM N-AMYL ALCOHOL BY EXTRACTIVE DISTILLATION

FIELD OF THE INVENTION

This invention relates to a method for separating n-amyl acetate from n-amyl alcohol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture n-amyl acetate is by the catalytic esterification of n-amyl alcohol with acetic acid. n-Amyl acetate (b.p.=148.4° C.), n-amyl alcohol (b.p.=138.1° C.) and water (b.p.=100° C.) form a minimum ternary azeotrope boiling at 94.8° C. and containing 10.5 weight percent n-amyl acetate, 33.3 wt. % n-amyl alcohol and 56.2 wt. % water. n-Amyl acetate forms a binary azeotrope with water boiling at 95.2° C. containing 59 wt. 2% n-amyl acetate. n-Amyl alcohol also forms a binary minimum azeotrope with water which boils at 95.8° C. and contains 45.6 wt. % n-amyl alcohol.

Thus in the esterification of n-amyl alcohol with acetic acid to form n-amyl acetate and water, the rectification of this mixture has two binary and a ternary azeotrope to contend with, and yields the lowest boiling constituent, namely the n-amyl acetate - n-amyl alcohol - water ternary azeotrope. It is therefore impossible to produce n-amyl acetate from n-amyl alcohol and water mixtures by rectification because the lower boiling ternary azeotrope will always come off overhead as the initial product. Any mixture of n-amyl acetate, n-amyl alcohol and water subjected to rectification at one atmosphere pressure will produce an overhead product boiling at 94.8° C. and containing 10.5 wt. % n-amyl acetate, 33.3 wt. % n-amyl alcohol and 56.2 wt. % water. Extractive distillation would be an attractive method of effecting the separation of n-amyl acetate from n-amyl alcohol if agents can be found that (1) will break the n-amyl acetate - n-amyl alcohol - water azeotrope and (2) are easy to recover from the n-amyl alcohol, that is, form no azeotrope with n-amyl alcohol and boil sufficiently above n-amyl alcohol to make the separation by rectification possible with only a few theoretical plates.

Extractive distillation typically requires the addition of an equal amount to twice as much extractive agent as the n-amyl acetate - n-amyl alcohol - water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with n-amyl alcohol otherwise it will form a two-phase azeotrope with the n-amyl alcohol in the recovery column and some other method of separation will have to be employed.

The breaking of this azeotrope by extractive distillation is a new concept. The closest applications of the concept might be the breaking of the methyl acetate - methanol azeotrope described by Berg & Yeh, CHEMICAL ENGINEERING COMMUNICATION, p.3219–3223 & 1984, U.S. Pat. Nos. 4,543,164 and 4,549,938. Berg & Ratanapupech, U.S. Pat. No. 4,379,028 separated ethyl acetate from ethanol. Berg & Yeh, U.S. Pat. Nos. 4,507,176 and 4,525,245 separated n-butyl acetate from n-butanol.

OBJECTIVE OF THE INVENTION

The object of this invention is to provide a process or method of extractive distillation that will enhance the relative volatility of n-amyl acetate from n-amyl alcohol in their separation in a rectification column. It is a further object of this invention to identify suitable extractive distillation agents which will eliminate the n-amyl acetate - n-amyl alcohol - water ternary azeotrope and make possible the production of pure n-amyl acetate and n-amyl alcohol by rectification. It is a further object of this invention to identify organic compounds which, in addition to the above constraints, are stable, can be separated from n-amyl alcohol by rectification with relatively few theoretical plates and can be recycled to the extractive distillation column and reused with little decomposition.

SUMMARY OF THE INVENTION

The objects of the invention are provided by a process for separating n-amyl acetate from n-amyl alcohol which entails the use of certain oxygenated organic compounds as the agent in extractive distillation.

DETAILED DESCRIPTION OF THE INVENTION

We have discovered that certain polyols comprising glycols and triols, some individually but principally as mixtures, will effectively negate the n-amyl acetate - n-amyl alcohol - water ternary azeotrope and permit the separation of pure n-amyl acetate from n-amyl alcohol by rectification when employed as the agent in extractive distillation. Table 1 lists the compounds, mixtures and approximate proportions that we have found to be effective. The data in Table 1 was obtained in a vapor-liquid equilibrium still. In each case, the starting material was the n-amyl acetate - n-amyl alcohol - water azeotrope. The ratios are the parts by weight of extractive agent used per part of n-amyl acetate - n-amyl alcohol - water azeotrope. The relative volatilities are listed for each of the two ratios employed. The compounds that are effective when used alone are ethylene glycol, propylene glycol, 1,3-butanediol, 1,4-butanediol, 1,5-pentanediol, 1,6-hexanediol, hexylene glycol, diethylene glycol, triethylene glycol, tetraethylene glycol, dipropylene glycol, polyethylene glycol and polypropylene glycol. The compounds which are effective when used in mixtures of two compounds or more are dimethylsulfoxide, dimethylformamide, acetamide, N,N-dimethylacetamide, 2-ethyl-1,3-hexanediol, 1,2,6-hexanetriol and glycerine. The two relative volatilities shown in Table 1 correspond to the two different ratios employed. For example, in Table 1, one part of ethylene glycol with one part of the n-amyl acetate - n-amyl alcohol - water azeotrope gives a relative volatility of 1.85, 6/5 parts of ethylene glycol give 2.13. One half part of propylene glycol mixed with one half part of dimethylsulfoxide with one part of the n-amyl acetate - n-amyl alcohol - water azeotrope gives a relative volatility of 2,04, 3/5 parts of propylene glycol plus 3/5 parts of DMSO gives 1.97.

TABLE 1

Extractive Distillation Agents Which Contain Glycols

| Compounds | Ratios | Relative Volatlities | |
|---|---|---|---|
| Ethylene glycol | 1  6/5 | 1.85 | 2.13 |
| Ethylene glycol, Dimethylsulfoxide (DMSO) | $(\frac{1}{2})^2$ $(3/5)^2$ | 1.81 | 2.17 |
| Ethylene glycol, Dimethylformamide (DMFA) | " | 2.07 | 2.05 |
| Ethylene glycol, N,N—Dimethylacetamide | " | 1.63 | 1.69 |
| Ethylene glycol, DMSO, DMFA | $(\frac{1}{3})^3$ $(2/5)^3$ | 2.14 | 2.23 |
| Ethylene glycol, DMSO, Acetamide | " | 2.03 | 1.82 |
| Ethylene glycol, N,N—Dimethylacetamide | " | 2.15 | 2.02 |
| Ethylene glycol, DMFA, Acetamide | " | 2.21 | 2.20 |
| Propylene glycol | 1 | 1.31 | — |
| Propylene glycol, DMSO | $(\frac{1}{2})^2$ $(3/5)^2$ | 2.04 | 1.97 |
| Propylene glycol, DMFA | " | 1.44 | 1.39 |
| Propylene glycol, DMSO, DMFA | $(\frac{1}{3})^3$ $(2/5)^3$ | 1.69 | 2.14 |
| Propylene glycol, DMSO, N,N—Dimethylacetamide | " | 1.64 | 1.60 |
| Propylene glycol, DMFA, Acetamide | " | 2.05 | 1.52 |
| 1,3-Butanediol | 1  6/5 | 1.46 | 1.51 |
| 1,3-Butanediol, DMSO | $(\frac{1}{2})^2$ $(3/5)^2$ | 2.36 | 1.75 |
| 1,3-Butanediol, DMFA | " | 1.66 | 1.76 |
| 1,3-Butanediol, DMSO, DMFA | $(\frac{1}{3})^3$ $(2/5)^3$ | 1.40 | 2.18 |
| 1,3-Butanediol, DMSO, N,N—Dimethylacetamide | " | 1.58 | 1.78 |
| 1,3-Butanediol, DMFA, Acetamide | " | 2.17 | 1.93 |
| 1,4-Butanediol | 1  6/5 | 2.40 | 2.13 |
| 1,4-Butanediol, DMSO | $(\frac{1}{2})^2$ $(3/5)^2$ | 1.74 | 1.69 |
| 1,4-Butanediol, DMFA | " | 1.91 | 2.02 |
| 1,4-Butanediol, DMSO, DMFA | $(\frac{1}{3})^3$ $(2/5)^3$ | 2.03 | 1.61 |
| 1,4-Butanediol, DMSO, N,N—Dimethylacetamide | " | 1.71 | 2.16 |
| 1,4-Butanediol, DMFA, Acetamide | " | 1.45 | 1.26 |
| 1,5-Pentanediol | 1  6/5 | 1.61 | 1.68 |
| 1,5-Pentanediol, DMSO | $(\frac{1}{2})^2$ $(3/5)^2$ | 1.96 | 1.37 |
| 1,5-Pentanediol, DMFA | " | 1.65 | 1.63 |
| 1,5-Pentanediol, DMSO, DMFA | $(\frac{1}{3})^3$ $(2/5)^3$ | 1.61 | 1.84 |
| 1,5-Pentanediol, DMSO, N,N—Dimethylacetamide | " | 1.80 | 1.97 |
| 1,6-Hexanediol | 1  6/5 | 1.49 | 1.44 |
| 1,6-Hexanediol, DMSO | $(\frac{1}{2})^2$ $(3/5)^2$ | 1.72 | 1.84 |
| 1,6-Hexanediol, DMFA | " | 1.73 | 1.59 |
| 1,6-Hexanediol, DMSO, DMFA | $(\frac{1}{3})^3$ $(2/5)^3$ | 1.53 | 1.37 |
| 1,6-Hexanediol, DMSO, N,N—Dimethylacetamide | " | 1.65 | 1.79 |
| 1,6-Hexanediol, DMFA, Acetamide | " | 1.70 | 1.66 |
| Hexylene glycol | 1 | 1.36 | — |
| Hexylene glycol, DMSO | $(\frac{1}{2})^2$ $(3/5)^2$ | 1.77 | 2.30 |
| Hexylene glycol, DMSO, DMFA | $(\frac{1}{3})^3$ $(2/5)^3$ | 1.92 | 1.91 |
| 2-Ethyl-1,3-hexanediol | 1 | 1.00 | |
| 2-Ethyl-1,3-hexanediol, DMSO | $(\frac{1}{2})^2$ $(3/5)^2$ | 1.38 | 1.47 |
| 2-Ethyl-1,3-hexanediol, DMFA | " | 1.25 | 1.25 |
| 2-Ethyl-1,3-hexanediol, DMSO, DMFA | $(\frac{1}{3})^3$ $(2/5)^3$ | 1.46 | 1.56 |
| 2-Ethyl-1,3-hexanediol, DMFA, Acetamide | " | 1.65 | 1.56 |
| Diethylene glycol | 1  6/5 | 1.83 | 1.79 |
| Diethylene glycol, DMSO | $(\frac{1}{2})^2$ $(3/5)^2$ | 1.39 | 1.10 |
| Diethylene glycol, DMFA | $(\frac{1}{2})^2$ — | 1.71 | |
| Diethylene glycol, DMSO, DMFA | $(\frac{1}{3})^3$ $(2/5)^3$ | 1.24 | 1.15 |
| Diethylene glycol, DMSO, N,N—Dimethylacetamide | " | 1.65 | 2.00 |
| Diethylene glycol, DMFA, Acetamide | $(\frac{1}{3})^3$ — | 1.53 | |
| Triethylene glycol | 1  6/5 | 1.79 | 1.77 |
| Triethylene glycol, DMSO | $(\frac{1}{2})^2$ $(3/5)^2$ | 1.98 | 2.17 |
| Triethylene glycol, DMFA | " | 1.80 | 1.75 |
| Triethylene glycol, DMSO, DMFA | $(\frac{1}{3})^3$ $(2/5)^3$ | 1.92 | 2.39 |

TABLE 1-continued

Extractive Distillation Agents Which Contain Glycols

| Compounds | Ratios | Relative Volatlities | |
|---|---|---|---|
| Triethylene glycol, DMSO, N,N—Dimethylacetamide | " | 1.55 | 1.99 |
| Triethylene glycol, DMFA, Acetamide | " | 2.10 | 2.31 |
| Tetraethylene glycol | 1 6/5 | 1.54 | 2.02 |
| Tetraethylene glycol, DMSO | $(\frac{1}{2})^2 (3/5)^2$ | 2.12 | 2.26 |
| Tetraethylene glycol, DMSO, DMFA | $(\frac{1}{3})^3 (2/5)^3$ | 2.09 | 1.48 |
| Tetraethylene glycol, DMSO, N,N—Dimethylacetamide | " | 1.74 | 1.61 |
| Dipropylene glycol | 1 6/5 | 1.50 | 1.48 |
| Dipropylene glycol, DMSO | $(\frac{1}{2})^2 (3/5)^2$ | 1.82 | 1.45 |
| Dipropylene glycol, DMFA | " | 1.50 | 1.67 |
| Dipropylene glycol, DMSO, DMFA | $(\frac{1}{3})^3 (2/5)^3$ | 1.41 | 1.82 |
| Dipropylene glycol, DMSO, N,N—Dimethylacetamide | " | 1.74 | 1.61 |
| Dipropylene glycol, DMFA, Acetamide | " | 2.51 | 1.73 |
| 1,2,6-Hexanetriol, DMSO, N,N—Dimethylacetamide | " | 1.63 | 1.69 |
| Polyethylene glycol | 1 6/5 | 1.61 | 1.95 |
| Polyethylene glycol, DMSO | $(\frac{1}{2})^2 (3/5)^2$ | 1.89 | 2.40 |
| Polyethylene glycol, DMFA | " | 1.67 | 1.99 |
| Polyethylene glycol, DMSO, DMFA | $(\frac{1}{3})^3 (2/5)^3$ | 2.23 | 2.65 |
| Polyethylene glycol, DMSO, N,N—Dimethylacetamide | " | 1.64 | 1.77 |
| Polyethylene glycol, DMFA, Acetamide | " | 2.34 | 2.69 |
| Polyethylene glycol, DMFA, N,N—Dimethylacetamide | " | 1.29 | 1.40 |
| Polypropylene glycol | 1 6/5 | 1.18 | 0.99 |
| Polypropylene glycol, DMSO | $(\frac{1}{2})^2 (3/5)^2$ | 1.74 | 1.93 |
| Polypropylene glycol, DMSO, DMFA | $(\frac{1}{3})^3 (2/5)^3$ | 1.72 | 1.72 |
| Polypropylene glycol, DMFA, Acetamide | " | 1.70 | 1.64 |
| Glycerine, DMSO | $(\frac{1}{2})^2 (3/5)^2$ | 2.10 | 2.11 |
| Glycerine, DMFA | " | 1.98 | 1.87 |
| Glycerine, DMSO, DMFA | $(\frac{1}{3})^3 (2/5)^3$ | 2.04 | 2.57 |
| Glycerine, DMSO, N,N—Dimethylacetamide | " | 1.72 | 1.91 |
| Glycerine, DMFA, Acetamide | " | 1.52 | 2.63 |

TABLE 2

Data From Run Made In Rectification Column

| Agent | Wt. % n-Amyl Acetate Overhead | Bottoms | Relative Volatility |
|---|---|---|---|
| Ethylene glycol | 83.33 | 9.09 | 2.39 |

Notes:
Ternary mixture comprised 22 wt. % n-amyl acetate, 71 wt. % n-amyl alcohol, 7 wt. % water.
Agent added at 20 ml/min. Reflux rate was 10-16 ml/min.

Ethylene glycol, one of the compounds listed in Table 1 whose relative volatility had been determined in the vapor-liquid equilibrium still, was then evaluated in a glass perforated plate rectification column possessing 4.5 theoretical plates. The n-amyl acetate - n-amyl alcohol-water mixture charged to the stillpot was 22 wt. % n-amyl acetate, 71 wt. % n-amyl alcohol and 7 wt. % water. The ratio of n-amyl acetate to n-amyl alcohol in the overhead is greater than 2.4 and the results are tabulated in Table 2. Without the extractive agent, the overhead would be the azeotrope whose ratio of n-amyl acetate to n-amyl alcohol is 2.4. This proves that the extractive agent is negating the azeotrope and makes the rectification proceed as if the azeotrope no longer existed and brings the more volatile components, n-amyl acetate and water, out as overhead products. It is our belief that this is the first time that this has been accomplished for this azeotrope.

The data in Table 2 was obtained in the following manner. The charge was 22% n-amyl acetate, 71% n-amyl alcohol and 7% water and after a half hour of operation in the 4.5 theoretical plate column to establish equilibrium, ethylene glycol at 95° C. and 10-16 ml/min was pumped in. The rectification was continued for about two hours with sampling of the overhead and bottoms after one hour, 1.5 hours and two hours. The average of the three analyses is shown in Table 2 and was 83.33% n-amyl acetate in the overhead and 9.09% in the bottoms, both on a water-free basis which gives a relative volatility of 2.39 of n-amyl acetate to n-amyl alcohol. This indicates that the ternary azeotrope has been negated and separation accomplished. The n-amyl acetate comes off in the form of its binary azeotrope with water which on condensation, immediately forms two layers. The solubility of n-amyl acetate in liquid water is only 0.1%.

THE USEFULNESS OF THE INVENTION

The usefulness or utility of this invention can be demonstrated by referring to the data presented in Table 1 and 2. All of the successful extractive distillation agents show that n-amyl acetate, n-amyl alcohol and water can be separated from their ternary azeotrope by means of distillation in a rectification column and that the ease of separation as measured by relative volatulity is considerable. Without these extractive distillation agents, no improvement above the azeotrope compostion will occur in the rectification column. The data also show that the most attractive agents will operate at a boilup rate low enough to make this a useful and efficient method of recovering high purity n-amyl acetate from any mixture of these three including the ternary azeotrope. The stability of the compounds used and the boiling point difference is such that complete recovery and recycle is obtainable by a simple distillation and the amount required for make-up is small.

WORKING EXAMPLES

Example 1

The n-amyl acetate - n-amyl alcohol - water azeotrope is 10.5 wt. % n-amyl acetate, 33.3 wt. % n-amyl alcohol and 56.2 wt. % water. Fifty grams of the n-amyl acetate - n-amyl alcohol - water azeotrope and fifty grams of ethylene glycol were charged to an Othmer type vapor-liquid equilibrium still and refluxed for 16 hours. Analysis of the vapor and liquid by gas chromatography gave a vapor composition of 14.2% n-amyl acetate, 81.3% n-amyl alcohol; a liquid composition of 8.4% n-amyl acetate, 88.5% n-amyl alcohol. This indicates a relative volatility of 1.85. Ten grams of ethylene glycol were added and refluxing continued for another eight hours. Analysis indicated a vapor composition of 14.1% n-amyl acetate, 82.1 % n-amyl alcohol; a liquid composition of 7.2% n-amyl acetate, 89.7% n-amyl alcohol which is a relative volatility of 2.13.

Example 2

Fifty grams of the n-amyl acetate - n-amyl alcohol - water azeotrope, 25 grams of propylene glycol and 25 grams of dimethylsulfoxide were charged to the vapor-liquid equilibrium still and refluxed for 18 hours. Analysis indicated a vapor composition of 21.5% n-amyl acetate, 64.7% n-amyl alcohol; a liquid composition of 12.5% n-amyl acetate, 76.6% n-amyl alcohol which is a relative volatility of 2.04. Five grams of propylene glycol and five grams of DMSO were added and refluxing continued for another nine hours. Analysis indicated a vapor composition of 19.4% n-amyl acetate, 66.1% n-amyl alcohol; a liquid composition of 11.5% n-amyl acetate, 77% n-amyl alcohol which is a relative volatility of 1.97.

Example 3

Fifty grams of the n-amyl acetate - n-amyl alcohol - water azeotrope, 17 grams of 1,3-butanediol, 17 grams of dimethylformamide and 17 grams of acetamide were charged to the vapor-liquid equilibrium still and refluxed for 12 hours. Analysis indicated a vapor composition of 24.3 n-amyl acetate, 53.6% n-amyl alcohol; a liquid composition of 14.9% n-amyl acetate, 71.2% n-amyl alcohol which is a relative volatility of 2.17. Three grams each of 1,3-butanediol, DMFA and acetamide were added and refluxing continued for another ten hours. Analysis indicated a vapor composition of 23.4% n-amyl acetate, 54% n-amyl alcohol; a liquid composition of 15.4% n-amyl acetate, 68.4% n-amyl alcohol which is a relative volatility of 1.93.

Example 4

A glass perforated plate rectification column was calibrated with ethylbenzene and p-xylene which possesses a relative volatility of 1.06 and found to have 4.5 theoretical plates. A solution comprising 88 grams of n-amyl acetate, 285 grams of n-amyl alcohol and 28 grams of water was placed in the stillpot and heated. When refluxing began, an extractive agent consisting of pure ethylene glycol was pumped into the column at a rate of 20 ml/min. The temperature of the extractive agent as it entered the column was 95° C. After establishing the feed rate of the extractive agent, the heat input to the n-amyl acetate - n-amyl alcohol - water in the stillpot was adjusted to give a total reflux rate of 10–16 ml/min. After one hour of steady operation, the overhead and bottoms samples of approximately two ml. were collected and analysed using gas chromatography. The overhead analysis was 83.33% n-amyl acetate, 16.67% n-amyl alcohol. The bottoms analysis was 9.09% n-amyl acetate, 90.91% n-amyl alcohol. Using these compositions in the Fenske equation, with the number of theoretical plates being 4.5, gave an average relative volatility of 2.39 for each theoretical plate.

The nature of the present invention having been described, what we wish to claim as new and useful and secure by Letters Patent is:

1. A method for recovering n-amyl acetate from a mixture of n-amyl acetate, n-amyl alcohol and water which comprises distilling a mixture of n-amyl acetate, n-amyl alcohol and water in a rectification column in the presence of about one part of extractive agent per part of n-amyl acetate - n-amyl alcohol - water mixture, recovering n-amyl acetate and water as overhead product and obtaining the n-amyl alcohol and the extractive agent from the stillpot, the extractive agent comprises at least a glycol.

2. The method of claim 1 in which the extractive agent comprises ethylene glycol.

3. The method of claim 1 in which the extractive agent comprises propylene glycol.

4. The method of claim 1 in which the extractive agent comprises 1,3-butanediol.

5. The method of claim 1 in which the extractive agent comprises 1,4-butanediol.

6. The method of claim 1 in which the extractive agent comprises 1,5-pentanediol.

7. The method of claim 1 in which the extractive agent comprises 1,6-hexanediol.

8. The method of claim 1 in which the extractive agent comprises hexylene glycol.

9. The method of claim 1 in which the extractive agent comprises diethylene glycol.

10. The method of claim 1 in which the extractive agent comprises triethylene glycol.

11. The method of claim 1 in which the extractive agent comprises tetraethylene glycol.

12. The method of claim 1 in which the extractive agent comprises dipropylene glycol.

13. The method of claim 1 in which the extractive agent comprises polyethylene glycol.

14. The method of claim 1 in which the extractive agent comprises polypropylene glycol.

15. The method of claim 1 in which the extractive agent comprises a mixture of ethylene glycol and at least one material from the group consisting of dimethylsulfoxide, dimethylformamide, acetamide and N,N-dimethylacetamide.

16. The method of claim 1 in which the extractive agent comprises a mixture of propylene glycol and at least one material from the group consisting of dimethylsulfoxide, dimethylformamide, acetamide and N,N-dimethylacetamide.

17. The method of claim 1 in which the extractive agent comprises a mixture of 1,3-butanediol and at least one material from the group consisting of dimethylsulfoxide, dimethylformamide, acetamide and N,N-dimethylacetamide.

18. The method of claim 1 in which the extractive agent comprises a mixture of 1,4-butanediol and at least one material from the group consisting of dimethylsulfoxide, dimethylformamide, acetamide and N,N-dimethylacetamide.

19. The method of claim 1 in which the extractive agent comprises a mixture of 1,5-pentanediol and at least one material from the group consisting of dimethylsulfoxide, dimethylformamide and N,N-dimethylacetamide.

20. The method of claim 1 in which the extractive agent comprises a mixture of 1,6-hexanediol and at least one material from the group consisting of dimethylsulfoxide, dimethylformamide, acetamide and N,N-dimethylacetamide.

21. The method of claim 1 in which the extractive agent comprises a mixture of hexylene glycol and at least one material from the group consisting of dimethylsulfoxide and dimethylformamide.

22. The method of claim 1 in which the extractive agent comprises a mixture of 2-ethyl-1,3-hexanediol and at least one material from the group consisting of dimethylsulfoxide, dimethylformamide and acetamide.

23. The method of claim 1 in which the extractive agent comprises a mixture of diethylene glycol and at least one material from the group consisting of dimethylsulfoxide, dimethylformamide, acetamide and N,N-dimethylacetamide.

24. The method of claim 1 in which the extractive agent comprises a mixture of triethylene glycol and at least one material from the group consisting of dimethylsulfoxide, dimethylformamide, acetamide and N,N-dimethylacetamide.

25. The method of claim 1 in which the extractive agent comprises a mixture of tetraethylene glycol and at least one material from the group consisting of dimethylsulfoxide, dimethylformamide and N,N-dimethylacetamide.

26. The method of claim 1 in which the extractive agent comprises a mixture of dipropylene glycol and at least one material from the group consisting of dimethylsulfoxide, dimethylformamide, acetamide and N,N-dimethylacetamide.

27. The method of claim 1 in which the extractive agent comprises a mixture of polyethylene glycol and at least one material from the group consisting of dimethylsulfoxide, dimethylformamide, acetamide and N,N-dimethylacetamide.

28. The method of claim 1 in which the extractive agent comprises a mixture of polypropylene glycol and at least one material from the group consisting of dimethylsulfoxide, dimethylformamide and acetamide.

29. A method for recovering n-amyl acetate from a mixture of n-amyl acetate, n-amyl alcohol and water which comprises distilling a mixture of n-amyl acetate, n-amyl alcohol and water in a rectification column in the presence of about one part of extractive agent per part of n-amyl acetate - n-amyl alcohol - water mixture, recovering n-amyl acetate and water as overhead product and obtaining the n-amyl alcohol and the extractive agent from the stillpot, the extractive agent comprises a mixture of glycerine and at least one material from the group consisting of dimethylsulfoxide, dimethylformamide, acetamide and N,N-dimethyl-acetamide.

30. A method for recovering n-amyl acetate from a mixture of n-amyl acetate, n-amyl alcohol and water which comprises distilling a mixture of n-amyl acetate, n-amyl alcohol and water in a rectification column the presence of about one part of extractive agent per part of n-amyl acetate - n-amyl alcohol - water mixture, recovering n-amyl acetate and water as overhead product and obtaining the n-amyl alcohol and the extractive agent from the stillpot, the extractive agent comprises a mixture of 1,2,6-hexanetriol, dimethylsulfoxide and N,N-dimethyl-acetamide.

* * * * *